United States Patent
Kim et al.

(10) Patent No.: US 12,410,091 B2
(45) Date of Patent: Sep. 9, 2025

(54) BIOACTIVE CRYSTALLIZED GLASS CERAMIC COMPRISING WOLLASTONITE, HYDROXYAPATITE AND DIOPSIDE, AND USE THEREOF

(71) Applicant: CG BIO CO., LTD., Gyeonggi-do (KR)

(72) Inventors: Baek-Hyun Kim, Seoul (KR); Hyun Seung Ryu, Gyeonggi-do (KR); Jun Hyuk Seo, Gyeonggi-do (KR); Seok Beom Song, Gyeonggi-do (KR)

(73) Assignee: CG BIO CO., LTD., Gyeonggi-do (KR)

( * ) Notice: Subject to any disclaimer, the term of this patent is extended or adjusted under 35 U.S.C. 154(b) by 872 days.

(21) Appl. No.: 17/637,045

(22) PCT Filed: Aug. 22, 2019

(86) PCT No.: PCT/KR2019/010665
§ 371 (c)(1),
(2) Date: Feb. 21, 2022

(87) PCT Pub. No.: WO2021/033803
PCT Pub. Date: Feb. 25, 2021

(65) Prior Publication Data
US 2022/0281767 A1  Sep. 8, 2022

(51) Int. Cl.
*C03C 10/00* (2006.01)
*A61L 27/04* (2006.01)
(Continued)

(52) U.S. Cl.
CPC ........ *C03C 10/0054* (2013.01); *A61L 27/047* (2013.01); *A61L 27/10* (2013.01);
(Continued)

(58) Field of Classification Search
CPC . C03C 10/00; C03C 10/0009; C03C 10/0054; C03C 4/0007; C03C 4/0021; A61L 27/10; A61L 27/12
See application file for complete search history.

(56) References Cited

U.S. PATENT DOCUMENTS

2005/0079226 A1  4/2005  Gonda et al.
2018/0028716 A1*  2/2018  Ryu .................. A61L 27/12

FOREIGN PATENT DOCUMENTS

EP  3225598 A1  10/2017
JP  2005-066354 A  3/2005
(Continued)

OTHER PUBLICATIONS

Shi. Characterization of natural hydroxyapatite originated from fish bone and its biocompatibility with osteoblasts. Materials Science and Engineering: C vol. 90, Sep. 1, 2018, pp. 706-712 (Year: 2018).*

(Continued)

*Primary Examiner* — Matthew E. Hoban
(74) *Attorney, Agent, or Firm* — pH IP Law

(57) ABSTRACT

The present invention relates to a glass ceramic composition comprising $SiO_2$, $Ca(OH)_2$, $CaF_2$, $B_2O_3$, MgO, and hydroxyapatite; a bioactive crystallized glass ceramic comprising each of $CaSiO_3$, $Ca_{10}(PO_4)_6(OH)_2$, and $CaMgSi_2O_6$ in an amount of 20% to 60% by weight; an implant for early osseointegration comprising the glass ceramic; and a method for manufacturing the implant.

6 Claims, 7 Drawing Sheets

(51) Int. Cl.
- *A61L 27/10* (2006.01)
- *A61L 27/12* (2006.01)
- *A61L 27/42* (2006.01)
- *A61L 27/50* (2006.01)
- *C03C 4/00* (2006.01)
- *C03B 32/02* (2006.01)

(52) U.S. Cl.
CPC ............. *A61L 27/12* (2013.01); *A61L 27/425* (2013.01); *A61L 27/427* (2013.01); *A61L 27/50* (2013.01); *C03C 4/0007* (2013.01); *A61L 2430/38* (2013.01); *C03B 32/02* (2013.01); *C03C 2204/00* (2013.01)

(56) References Cited

FOREIGN PATENT DOCUMENTS

| | | |
|---|---|---|
| JP | 2014-512325 A | 5/2014 |
| KR | 10-2009-0035649 A | 11/2002 |
| KR | 1-2009-0037889 A | 6/2007 |
| KR | 10-2014-0014354 A | 4/2010 |
| KR | 10-1724592 B1 | 5/2015 |
| KR | 10-2018-0056370 A | 11/2017 |

OTHER PUBLICATIONS

Bellucci, D. et al., "Bone Regeneration by Novel Bioactive Glasses Containing Strontium and/or Magnesium: A Preliminary In-Vivo Study", Materials 2018, 11, 2223.

Kokubo, T. et al., "Mechanical Properties of a New Type of Apaptite-Containing Glass-Ceramic for Prosthetic Application", Journal of Materials Science, 1985, pp. 2001-2004.

Kurtz, S. and Devine, J, "PEEK Biomaterials in Trauma, Orthopedic, and Spinal Implants", Biomaterials 28, pp. 4845-4869.

Extended European Search Report issued in European Patent Application No. 19941940.9, dated May 2, 2023.

* cited by examiner

[Fig. 1]
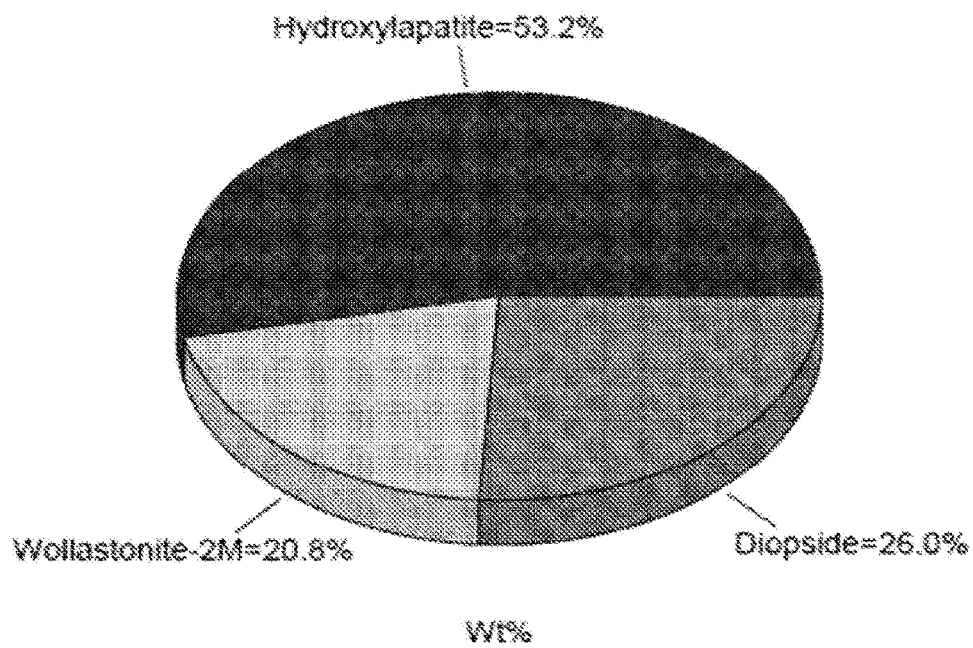

[Fig. 2]
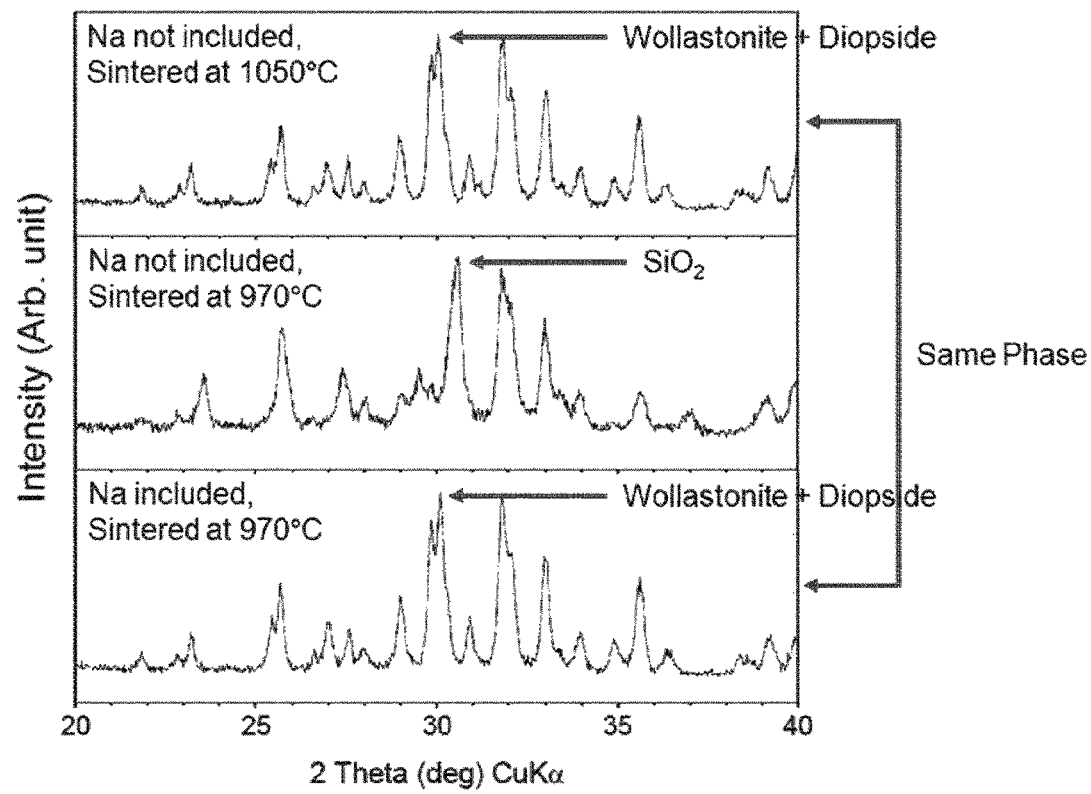
[Fig. 3]
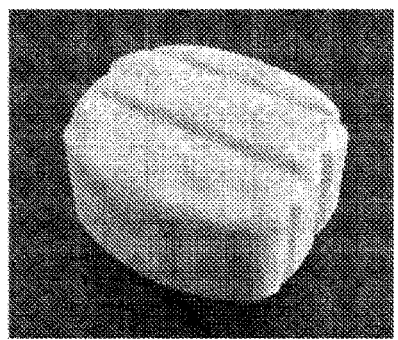

[Fig. 4]
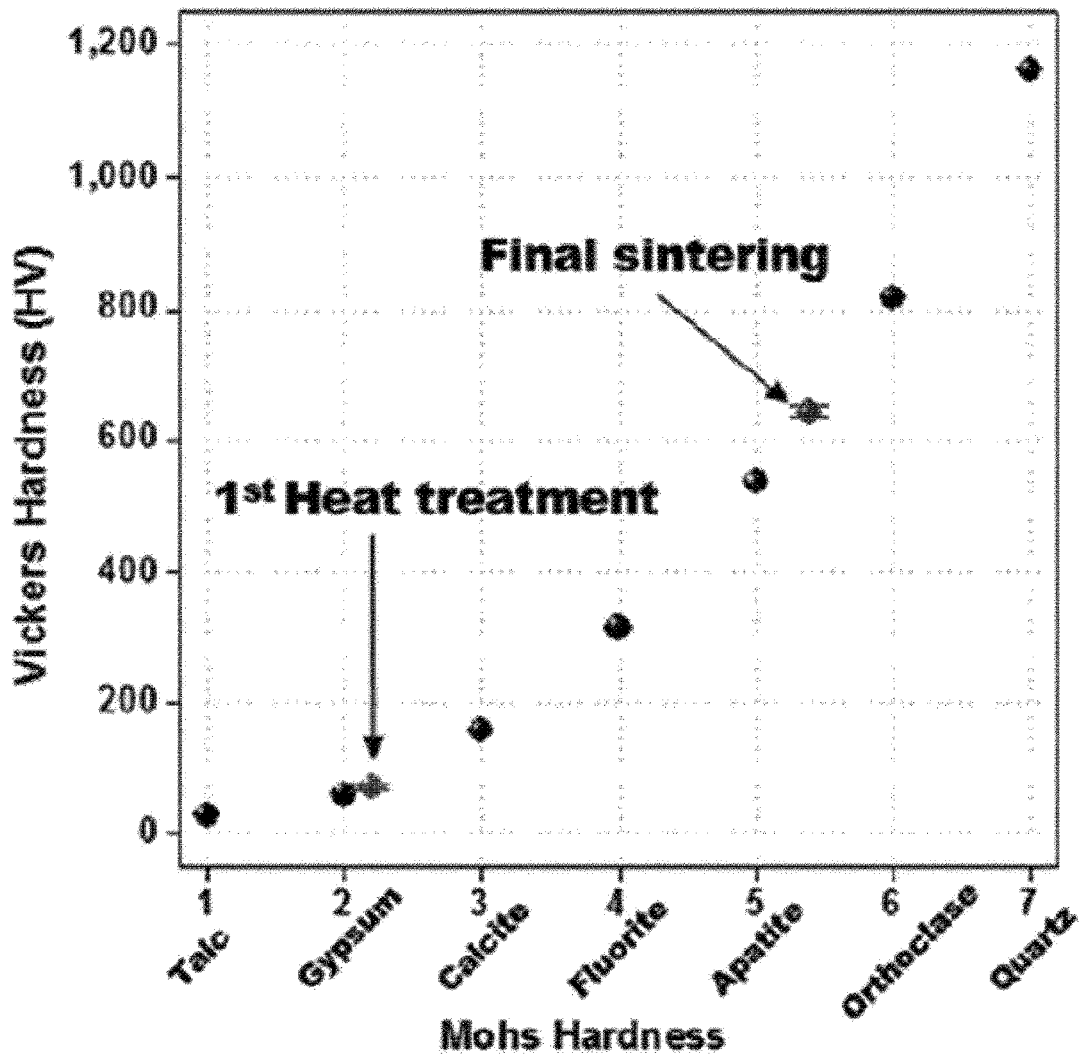

[Fig. 5]
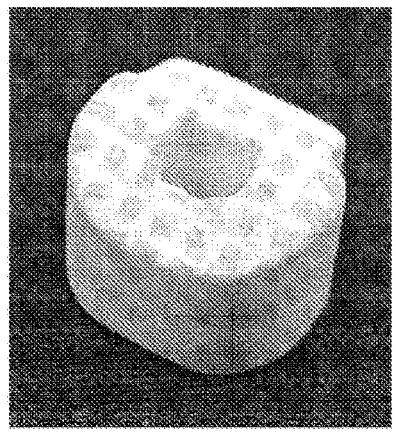
[Fig. 6a]
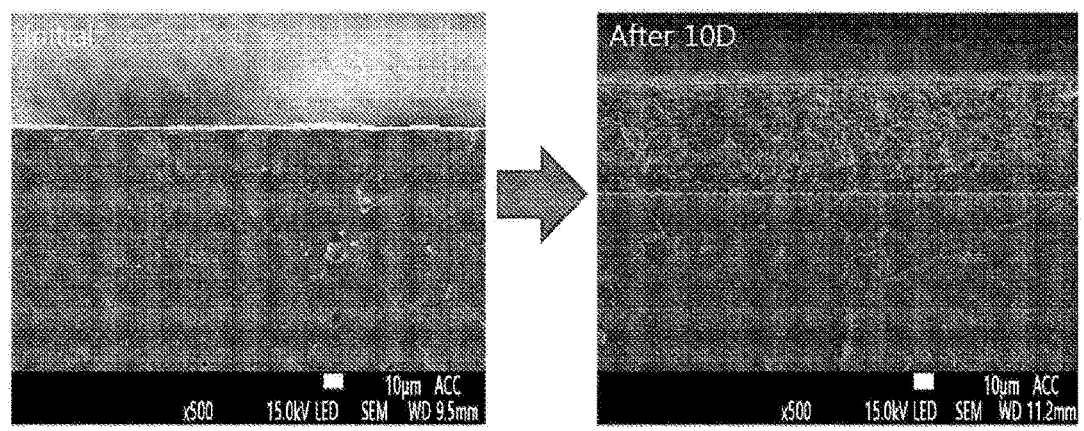

[Fig. 6b]
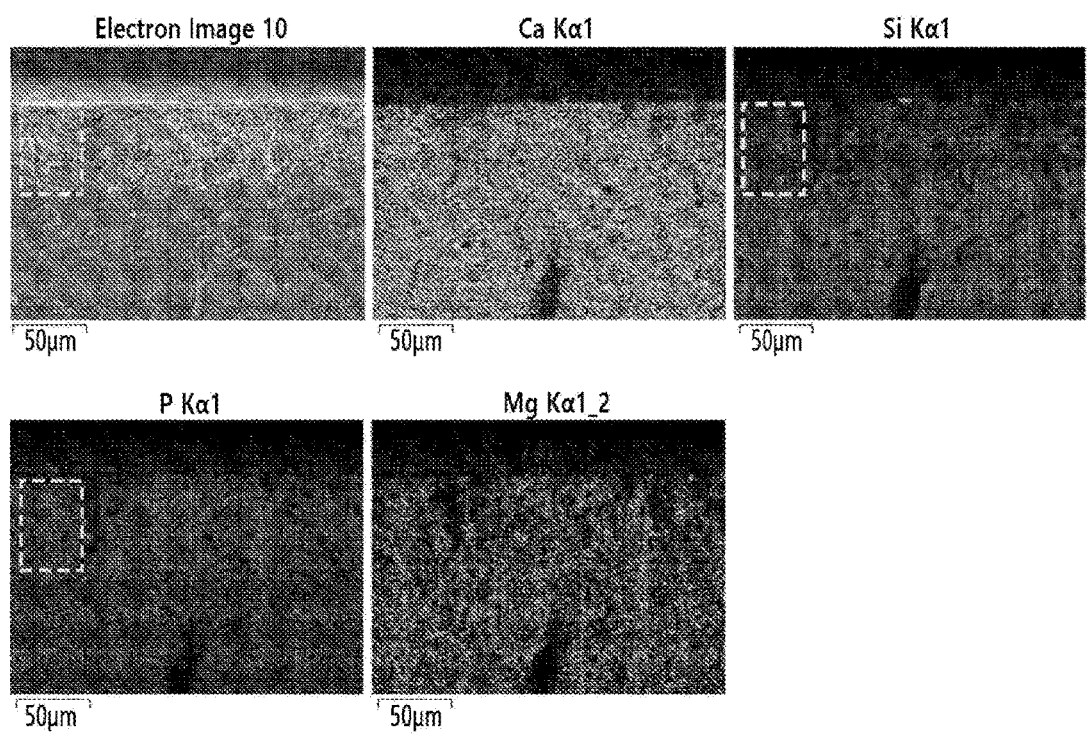

[Fig. 6c]
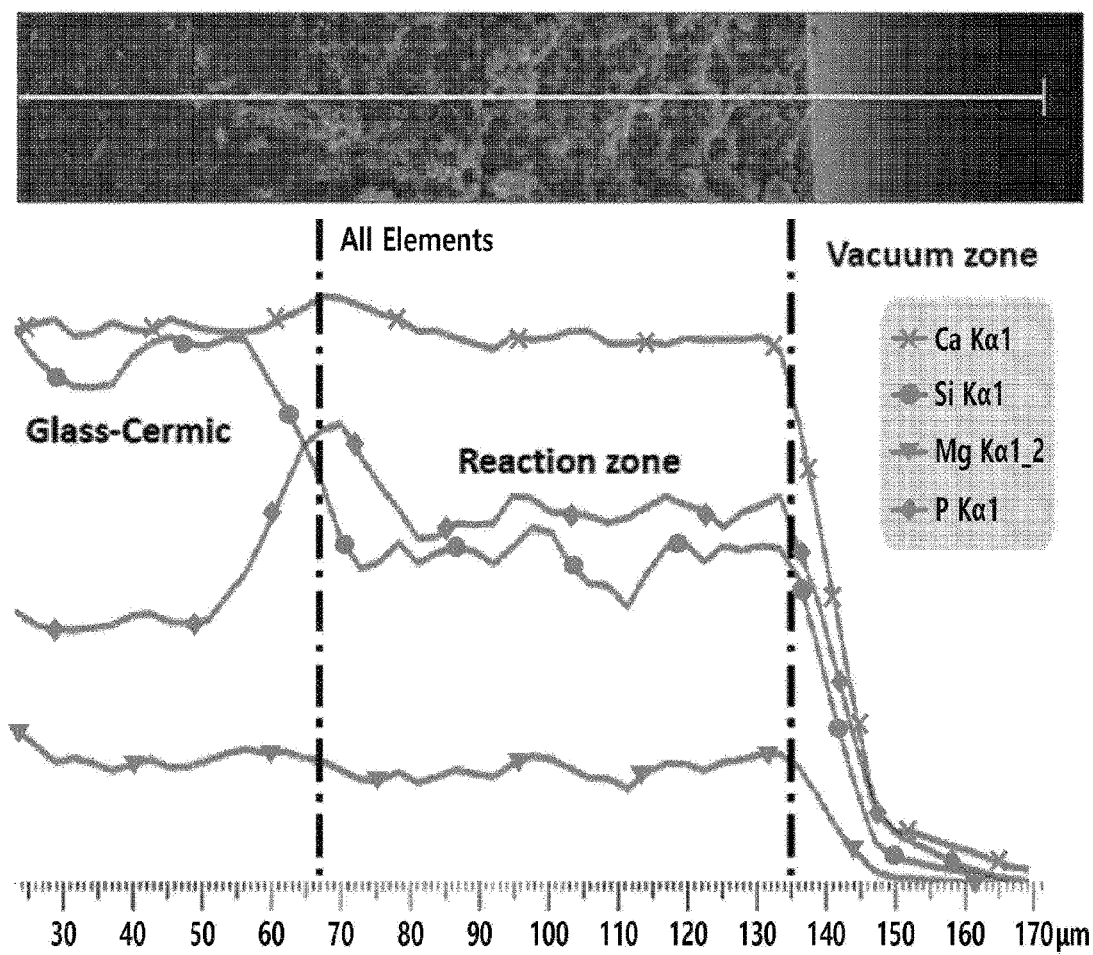

[Fig. 6d]
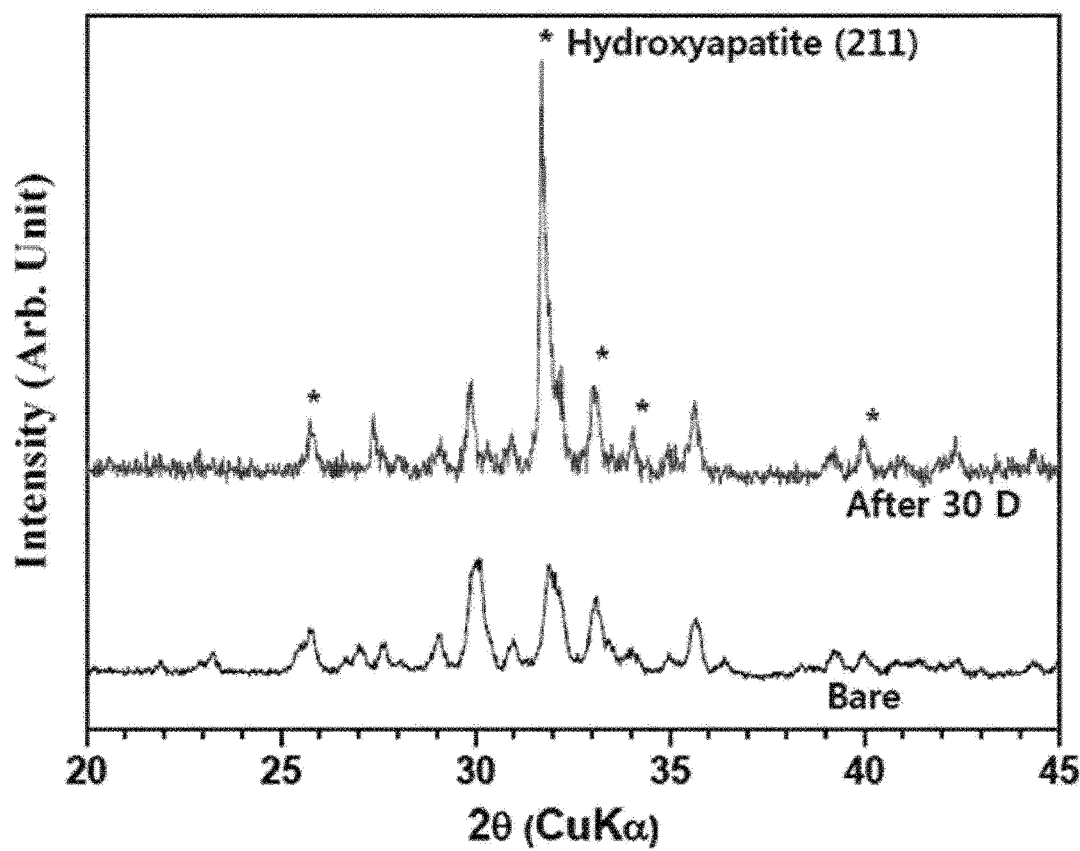

BIOACTIVE CRYSTALLIZED GLASS CERAMIC COMPRISING WOLLASTONITE, HYDROXYAPATITE AND DIOPSIDE, AND USE THEREOF

This application is a national phase application under 35 U.S.C. § 371 of International Application No. PCT/KR2019/010665, filed Aug. 22, 2019. The entire text of the above referenced disclosure is specifically incorporated herein by reference.

TECHNICAL FIELD

The present invention relates to a glass ceramic composition including $SiO_2$, $Ca(OH)_2$, $CaF_2$, $B_2O_3$, MgO, and hydroxyapatite; a bioactive crystallized glass ceramic including each of $CaSiO_3$, $Ca_{10}(PO_4)_6(OH)_2$, and $CaMgSi_2O_6$ in an amount of 20% to 60% by weight; an implant for early osseointegration including the glass ceramic; and a method for manufacturing the implant.

BACKGROUND ART

Spinal stenosis refers to a complex neurotic disease caused by narrowing of the spinal canal, neural canal, or intervertebral foramen, leading to back pain or cervical pain, or pain in the arms or legs. In particular, the spinal canal is a tubular hollow space in the middle of the spine, the intervertebral foramina are present in the upper and lower spine, and the middle part of the spinal canal forms the space through which nerves (the spinal cord) pass from the brain to the limbs. The spinal canal is in an oval or triangular shape, and is largest in the cervical region, narrowing in the thoracic region, and widening again in the lumbar region and narrowing downward.

When spinal stenosis occurs in the lumbar spine, it is called lumbar spinal stenosis, and when it occurs in the cervical spine, it is called cervical canal stenosis.

Lumbar spinal stenosis refers to a medical condition in which the spinal canal or neural tube that encompasses the spinal cord is compressed by a bone or ligament enlarged due to a degenerative change. Such an enlarged bone or ligament presses the nerve that passes through the lumbar spinal canal, thereby causing lower back pain or leg pain.

Cervical canal stenosis refers to a spinal canal stenosis that occurs in the cervical vertebrae, and it compresses the nerves passing through the cervical canal due to degenerative changes in the spinal canal or neural tube, causing cervical pain or pain in the arms or legs.

Although non-surgical treatment may be performed as a primary treatment for the above diseases, spinal stenosis not responding to non-surgical treatment for a certain period of time can fundamentally be treated only via surgical operation. Therefore, surgical treatment must be considered in patients who have disease that has progressed considerably, and thus do not show any significant effect with conservative therapies, or in patients who have many limitations in their daily lives or have acute severe symptoms accompanied by a disc disease.

Examples of the surgical methods of treating the diseases may include an intervertebral fusion. The fusion is an operation for removing the movement between the segments through the fusion of the graft bone and the host bone, and maintaining its continuous and strong stability.

Meanwhile, there are a number of processes that are affected by various physical and biological environments until the graft bone is fused with the host bone. Accordingly, the graft material mainly used for bone integration is autogenous bone, but there are many limitations.

Material such as metals, ceramics, polymers, etc. are currently used for bone integration. The materials may be selected considering the strength, durability, biocompatibility, in vivo stability, osteoconductivity, ease of processability, disinfection/sterilization stability, etc. Additionally, it is important that the materials be provided with magnetic permeability, radiolucency, and appropriate hardness.

Metals such as titanium, etc. have excellent biocompatibility and high strength, but have a disadvantage in they require a separate bone graft material such as autologous bone or demineralized bone matrix (DBM) due to their low osteoconductivity. Additionally, metals have an extremely high modulus of elasticity, and thus may cause a stress shielding effect or subsidence of the bones (V. H. CIA et al., 2017).

Meanwhile, polymers such as PEEK have advantages in that they have high strength, low risk of fracture, and an appropriate modulus of elasticity, but have disadvantages in that they have significantly low osteoconductivity compared to ceramics such as hydroxyapatite or metals such as titanium, etc. and thus require a separate bone graft material, and in that they have high radiation transparency and thus require separate treatment (metal spikes, etc.) for follow-up observations (S. M. Kurtz et al., 2007). Ceramics such as hydroxyapatite (HA) or bioglass, etc. have high biocompatibility and osteoconductivity, but have a high risk of fracture due to low strength and brittleness, and thus, it may be difficult to use them alone (D. Bellucci et al., 2018).

DISCLOSURE

Technical Problem

The present inventors have confirmed that the crystallized glass ceramic including wollastonite, hydroxyapatite, and diopside at an optimal ratio, which is crystallized by sintering a composition including $SiO_2$, $Ca(OH)_2$, $CaF_2$, $B_2O_3$, MgO, and hydroxyapatite at high temperature, not only shows significantly improved strength, but also exhibits excellent bioactivity compared to the conventional wollastonite/hydroxyapatite composite glass ceramic, thereby completing the present invention.

Technical Solution

One object of the present invention is to provide a glass ceramic composition including $SiO_2$, $Ca(OH)_2$, $CaF_2$, $B_2O_3$, MgO, and hydroxyapatite.

Another object of the present invention is to provide a bioactive crystallized glass ceramic including each of $CaSiO_3$, $Ca_{10}(PO_4)_6(OH)_2$, and $CaMgSi_2O_6$ in an amount of 20% to 60% by weight, which is prepared by sintering the glass ceramic composition.

Still another object of the present invention is to provide an implant including the crystallized glass ceramic.

Yet another object of the present invention is to provide a method for manufacturing the implant, including the steps of: preparing the glass ceramic composition; forming the glass ceramic composition; and heat-treating the formed glass ceramic composition.

Advantageous Effects

The present invention relates to a glass ceramic composition including $SiO_2$, $Ca(OH)_2$, $CaF_2$, $B_2O_3$, MgO, and hydroxyapatite; a bioactive crystallized glass ceramic including each of $CaSiO_3$, $Ca_{10}(PO_4)_6(OH)_2$, and $CaMgSi_2O_6$ in an amount of 20% to 60% by weight, which is prepared by sintering the glass ceramic composition; an implant including the glass ceramic; and a method for manufacturing the implant. Accordingly, the implant including the glass ceramic of the present invention has high bending strength and compressive strength, has excellent osseointegration ability, and can be used alone without a bone graft material, and thus is expected to be useful and convenient for treating spinal diseases such as spinal stenosis.

BRIEF DESCRIPTION OF DRAWINGS

FIG. 1 is a diagram showing the component ratio of XRD crystalline phases $CaSiO_3$, $Ca_{10}(PO_4)_6(OH)_2$, and $CaMgSi_2O_6$ of the crystallized glass ceramic of the present invention.

FIG. 2 is a diagram showing the XRD pattern of the glass ceramic according to the sintering temperature and the addition of Na.

FIG. 3 is a diagram showing the implant manufactured through grinding as a spinal implant including the glass ceramic of the present invention.

FIG. 4 is a diagram showing the hardness of the glass ceramic composition of the present invention after the first heat treatment and second heat treatment.

FIG. 5 is a diagram showing the spinal implant including the glass ceramic of the present invention, which is manufactured through CAD/CAM.

FIGS. 6a-6d. FIG. 6a is a diagram showing the body reaction effect according to the simulated body fluid (SBF) immersion test; FIG. 6a is a diagram showing the surface after 10 days of exposure to SBF; FIG. 6b is a diagram showing the EDS analysis results of the elements of the reaction layer formed on the surface through FE-SEM; FIG. 6c is a diagram showing an increase or decrease of Ca, Si, Mg, and P in the surface layer; and FIG. 6d is a diagram showing the XRD pattern after 30 days of exposure to SBF.

DETAILED DESCRIPTION OF PREFERRED EMBODIMENTS

The present invention will be described in detail as follows. Meanwhile, each description and embodiment disclosed herein can be applied to other descriptions and embodiments. That is, all combinations of various elements disclosed herein fall within the scope of the present invention. Further, the scope of the present invention is not limited by the specific description described below.

Additionally, those of ordinary skill in the art may be able to recognize or confirm, using only conventional experimentation, many equivalents to the particular aspects of the invention described herein. Furthermore, it is also intended that these equivalents be included in the present invention.

In order to achieve the objects above, one aspect of the present invention provides a glass ceramic composition including $SiO_2$, $Ca(OH)_2$, $CaF_2$, $B_2O_3$, MgO, and hydroxyapatite.

The composition may include $SiO_2$ in an amount of 15% to 45% by weight, $Ca(OH)_2$ in an amount of 20% to 45% by weight, $CaF_2$ in an amount of 0.01% to 5% by weight, $B_2O_3$ in an amount of 0.01% to 5% by weight of, MgO in an amount of 0.01% to 20% by weight, and hydroxyapatite in an amount of 15% to 45% by weight based on the total weight of the glass ceramic composition.

Specifically, the composition may include $SiO_2$ in an amount of 15% to 45% by weight, $Ca(OH)_2$ in an amount of 25% to 45% by weight, $CaF_2$ in an amount of 0.01% to 3.5% by weight, $B_2O_3$ in an amount of 0.01% to 3.5% by weight of, MgO in an amount of 0.01% to 20% by weight, and hydroxyapatite in an amount of 15% to 45% by weight based on the total weight of the glass ceramic composition.

More specifically, in the composition, $SiO_2$ may be contained in an amount of 17% to 43% by weight, 20% to 40% by weight, or 22% to 38% by weight, $Ca(OH)_2$ may be contained in an amount of 25% to 38% by weight, 26% to 36% by weight, or 28% to 34% by weight, $CaF_2$ may be contained in an amount of 0.05% to 3.5% by weight or 0.05% to 3% by weight, $B_2O_3$ may be contained in an amount of 0.01% to 3.5% by weight or 0.05% to 3% by weight, MgO may be contained in an amount of 0.5% to 14% by weight or 0.5% to 12% by weight, and hydroxyapatite may be contained in an amount of 18% to 42% by weight, 20% to 40% by weight, or 22% to 38% by weight.

In one embodiment of the present invention, the composition may include $SiO_2$ in an amount of 25% to 35% by weight, $Ca(OH)_2$ in an amount of 28% to 32% by weight, $CaF_2$ in an amount of 0.1% to 3.5% by weight, $B_2O_3$ in an amount of 0.05% to 2% by weight of, MgO in an amount of 1% to 10% by weight, and hydroxyapatite in an amount of 25% to 35% by weight based on the total weight of the glass ceramic composition.

The composition of the present invention may further include Na. The Na may be contained in an amount of 0.01% to 5% by weight based on the total weight of the glass ceramic composition, and specifically, it may be contained in an amount of 0.05% to 3% by weight, 0.1% to 2% by weight, or 0.1% to 1% by weight, but is not limited thereto.

In one specific embodiment of the present invention, in the case where Na is not added to the glass ceramic composition, wollastonite and diopside phases were not formed when heat-treated at 970° C., and the corresponding crystalline phases were formed only when heat-treated at 1050° C. However, wollastonite and diopside phases were formed even at 970° C. when Na was added. This suggests that the addition of Na may have a role of accompanying the formation of wollastonite and diopside phases even at low temperature. When Na is added, heat treatment is possible at low temperature, and thus, it is possible to overcome the problem of cracking caused by swelling or thermal expansion that may occur when the heat treatment temperature is high, and a desired shape can be easily formed at an optimum temperature.

In another specific embodiment of the present invention, the Na may be in the form of a metal or salt, and specifically, it may be $Na_2CO_3$, but is not limited thereto.

In still another specific embodiment of the present invention, it was confirmed that the crystallized glass ceramic of the present invention showed significantly high bending strength and compressive strength, compared to hydroxyapatite sintered bodies and apatite-wollastonite (AW) glass, a representative bioactive glass. Specifically, the bending strength of hydroxyapatite was 115 MPa and that of AW glass was 215 MPa, while it was confirmed that the bending strength of the crystallized glass ceramic of the present invention was 240 to 250 Mpa. Additionally, the compressive strength of hydroxyapatite was 830 MPa and that of AW glass was 1060 MPa, while it was confirmed that the compressive strength of the crystallized glass ceramic of the present invention was 1115 to 1320 MPa.

This suggests that the glass ceramic of the present invention has excellent physical properties of high strength.

Another aspect of the present invention provides a bioactive crystallized glass ceramic including each of $CaSiO_3$, $Ca_{10}(PO_4)_6(OH)_2$, and $CaMgSi_2O_6$ in an amount of 20% to 60% by weight, which is prepared by sintering the glass ceramic composition.

The $CaSiO_3$ is wollastonite, $Ca_{10}(PO_4)_6(OH)_2$ is hydroxyapatite (HA), and $CaMgSi_2O_6$ is diopside.

As used herein, the term "wollastonite" is a calcium inosilicate mineral represented by the chemical formula of $CaSiO_3$, which may contain small amounts of iron, magnesium, and manganese instead of calcium. Naturally, wollastonite may be formed when limestones or dolostones with impurities are subjected to high-temperature and high-pressure conditions in the presence of silica-bearing fluids, as in the cases of skarns or contact metamorphic rocks. The relevant minerals may include garnets, vesuvianite, diopside, tremolite, epidote, plagioclase feldspar, pyroxene, and calcite. For example, wollastonite may be produced by reaction between silica and calcite, which releases carbon dioxide.

Wollastonite can be used in ceramics, friction products such as brakes and clutches, metalmaking, paint fillers, and plastics.

As used herein, the term "hydroxyapatite" is a naturally-occurring mineral form of calcium apatite, which has the chemical formula of $Ca_5(PO_4)_3(OH)$, but it can normally be expressed as $Ca_{10}(PO_4)_6(OH)_2$ because the crystal unit cell contains two independent bodies. Hydroxyapatite refers to a single hydroxy component of a complex apatite group, and $OH^-$ ion may be substituted with fluoride, chloride, carbonate, etc., to form fluorapatite, chlorapatite, etc. Pure hydroxyapatite powder may be white, but natural apatite can be brown, yellow, or green. Hydroxyapatite may be formed naturally or by wet chemical deposition, biomimetic deposition, a sol-gel process which is also referred to as wet chemical precipitation, or electrodeposition.

Hydroxyapatite may be present in teeth and bone tissue in the human body. Accordingly, hydroxyapatite may be used as a filler replacing a cut bone tissue or as a coating agent to promote the in-growth of bone tissue into a prosthetic implant.

As used herein, the term "diopside" is a monoclinic concentrate volatile mineral with the chemical formula $CaMgSi_2O_6$. It can generally be pale green or blue, brown, colorless or white. It is subdivided into short prismatic crystals and exists in columnar shapes. It has distinct splits and irregular fractures, has a Mohs hardness of 5.5 to 6.5, and has a melting point of 1391° C. Glass ceramics containing diopside can be used in various technical fields, such as biomaterials, and fixing and sealing materials for nuclear waste.

The crystallized glass ceramic of the present invention may include each of $CaSiO_3$, $Ca_{10}(PO_4)_6(OH)_2$, and $CaMgSi_2O_6$ at a weight ratio of 20 to 60, specifically, at a weight ratio of 10 to 30:45 to 65:15 to 35, at a weight ratio of 15 to 25:50 to 60:20 to 30, or a weight ratio of 15 to 25:50 to 60:20 to 30, but is not limited thereto. It was confirmed that the crystallized glass ceramic including the composition above was rapidly converted to hydroxyapatite to form a reaction layer when exposed to a body fluid (Experimental Example 4-1), indicating that it has excellent osseointegration capability of early integration with bone.

The crystallized glass ceramic of the present invention may be a crystallized glass ceramic essentially consisting of $CaSiO_3$, $Ca_{10}(PO_4)_6(OH)_2$, and $CaMgSi_2O_6$. The crystallized glass ceramic essentially consisting of $CaSiO_3$, $Ca_{10}(PO_4)_6(OH)_2$, and $CaMgSi_2O_6$ includes $CaSiO_3$, $Ca_{10}(PO_4)_6(OH)_2$, and $CaMgSi_2O_6$, which may mean to include less than 10%, less than 8%, less than 5%, less than 3%, or less than 1% of other crystalline phases based on the total weight of the crystallized glass ceramic.

The crystallized glass ceramic may not substantially include $Ca_2Mg(Si_2O_7)$ and may include $CaMgSi_2O_6$ at a weight ratio of 20 to 60, at a weight ratio of 15 to 35, or at a weight ratio of 20 to 30 based on 100 weight ratio of the crystalline phase of the glass ceramic. In this case, a reaction layer is formed more rapidly when exposed to a body fluid, and thus excellent osteointegration capability can be achieved.

The crystallized glass ceramic of the present invention may have a crystallinity of 25% or more or 50% or more. More specifically, the crystallinity may be 80% or more, 82% or more, 84% or more, 86% or more, 88% or more, 90% or more, 92% or more, 94% or more, 95% or more, 96% or more, 98% or more, 99% or more, or 100%, and may be any combination within these ranges, but is not limited thereto.

The crystallized glass ceramic of the present invention may be formed by sintering at a temperature of 900 to 1100° C., specifically 900 to 1050° C., and more specifically 900 to 1000° C. If the sintering temperature is 900° C. or less, crystallization may occur insufficiently or breakage may occur due to interruption of crystallization, so it may not be possible to be used as a product. Meanwhile, sintering at a temperature exceeding 1100° C. is not only accompanied by energy waste due to unnecessary heating, but also the shape of the crystallized glass ceramic may be distorted, for example, the middle part of the crystallized glass ceramic may be protruded.

In the present invention, the glass ceramic may be synthesized by further adding Na to the glass ceramic composition and sintering at a lower temperature. In one specific embodiment of the present invention, when a glass ceramic composition not containing Na was used, $SiO_2$ was phase-transformed into wollastonite and diopside only when sintered at a relatively high temperature of 1050° C. Meanwhile, when the glass ceramic composition containing Na was used, it was confirmed that the wollastonite and diopside phases were formed even when sintered at a relatively low temperature of 970° C.

When the crystallized glass ceramic of the present invention is exposed to a body fluid, it can integrate with bone with excellent bioactivity. Although not delineated in any particular theory, when the glass ceramic is in contact with a body fluid, $Ca^{2+}$ ions and $PO_4^{3-}$ ions are eluted from the glass ceramic, and CaP clusters are formed by supersaturation of the ions. As the CaP cluster binds to the Si—O—H group present in the crystallized glass ceramic, bone-like apatite can be formed on the surface of the crystallized glass ceramic. The crystallized glass ceramic may have a mechanism of integrating with bone through the apatite formed as described above.

In one specific embodiment of the present invention, as a result of the simulated body fluid (SBF) immersion test, it was confirmed that a gray reaction layer with a thickness of 69 μm was formed on the surface after 10 days, and that it was converted to apatite which was confirmed by an increase in P and a decrease in Si in the surface layer (Experimental Example 4-1). Among the crystalline phases of wollastonite ($CaSiO_3$), hydroxyapatite ($Ca_{10}(PO_4)_6(OH)_2$) and diopside ($CaMgSi_2O_6$) present in crystallized glass ceramics, considering that other crystalline phases do not contain P, except apatite, these results indicate that apatite was formed in the reaction layer, which was confirmed by an increase in P and a decrease in Si in the reaction layer formed on the surface. Further, after 30 days, as a result of confirming the XRD patterns, an increase in the peak of hydroxyapatite was clearly observed, indicating that apatite was formed in the reaction layer.

Through such a series of experiments, it was confirmed that the crystallized glass ceramic of the present invention has excellent surface apatite forming ability, which suggests that the crystallized glass ceramic of the present invention will exhibit excellent osseointegration ability.

Still another aspect of the present invention provides a method for manufacturing a bioactive crystallized glass ceramic using the glass ceramic composition.

Specifically, the composition may be prepared at a temperature of 900 to 1100° C. In addition, when Na is added, the composition may be prepared by heat treatment at a low temperature of 900 to 1000° C. When Na is added, heat treatment can be performed at a low temperature, and thus, the problem of swelling or cracking that occurs when heat treatment is performed at a high temperature can be overcome, and the composition may be easily processed into a desired shape at an optimum temperature.

Yet another aspect of the present invention provides an implant including the above-described crystallized glass ceramic.

Examples of the international test standards related to the physical/mechanical evaluation of the implant may include ASTM F2077, ASTM F2267, etc. Among them, the former specifies the experimental environment including the jig for the static compression and torsion test and the dynamic fatigue test, and provides related test protocols.

The implant may have a compressive strength of 5 to 20 kN, a torsional strength of 3 to 10 Nm, and a fatigue compressive strength which can withstand a fatigue load of 3 kN until 5,000,000 cycles without breaking, when measured by way of the ASTM F2077-18 method.

In one specific embodiment of the present invention, it was confirmed that the implant manufactured by a grinding manufacturing method exhibited the physical properties of a compressive strength of 10 to 20 kN, a torsional strength of 5 to 10 Nm, and a fatigue compressive strength which can withstand a fatigue load of 3 kN until 5,000,000 cycles without breaking, which exceeded the target values.

In another specific embodiment of the present invention, it was confirmed that the implant manufactured by CAD/CAM had the physical properties of a compressive strength of 5 to 15 kN, a torsional strength of 3 to 7 Nm, and a fatigue compressive strength which can withstand a fatigue load of 3 kN until 5,000,000 cycles without breaking.

Therefore, the implant of the present invention can be used for early osseointegration of the cervical spine and lumbar spine requiring higher strength.

As used herein, the term "compressive strength" refers to the maximum stress of a material which can withstand a compressive load. The compressive strength of materials that are broken into pieces upon compression may be defined as an independent nature in a narrow sense, but the compressive strength of materials that are not broken into pieces upon compression may be defined by the amount of stress required to deform any material with a random quantity. The measurement may be made by plotting the force applied to a test device against the deformation. In compression tests, the compressive strength may be calculated by dividing the maximum load by the initial cross-sectional area of the specimen.

As used herein, the term "torsional strength or torsion" refers to the degree of capability of a material to withstand a torsional load, in which the torsional strength is the maximum strength of the material subjected to the torsional load, and may be the maximum torsional stress that can maintain the material before fracture. The term is also referred to as modulus of fracture or shear strength. As the measurement unit, Newton meter (N·m) or feet pound force (ft·lbf) may be used.

As used herein, the term "fatigue strength" refers to the amount of fluctuating stress required for the fracture of a fatigue test specimen by applying a predetermined number of repeated loads, in which the number of repetitions is called fatigue life. Fatigue strength can generally be measured directly from the S-N curve, but is not limited thereto. ASTM defines fatigue strength ($S_{Nf}$) as the stress value at which the fracture of the number of $N_f$ cycles occurs.

The implant of the present invention may be used alone without a bone graft material.

In one specific embodiment of the present invention, it was confirmed that the implant was osseointegrated with a ratio of 91% vs 90% compared to the titanium implant with autogenous bone. This suggests that the implant for osseointegration including the glass ceramic of the present invention can be osseointegrated at an excellent rate even when used alone without a bone graft material.

Meanwhile, implant bonding can act as three main parameters: friction, mechanical bonding, and chemical bonding. The biocompatibility of titanium alloys allows bone growth to reach close to the titanium surface, which forms a mechanical bond due to local properties such as roughness and porosity of the surface. However, titanium cannot be chemically bonded to bone, and thus cannot be strongly bonded to bone due to the smooth surface of the titanium implant and local support.

Hydroxyapatite and calcium phosphate-based materials are ideal materials because they do not show a foreign body reaction and can be strongly bonded to bone on the surface. After it was reported that hydroxyapatite and beta-tricalcium phosphate (β-TCP) chemically and strongly bind to bone, many studies have been conducted on the mechanism of bone bonding between hydroxyapatite and calcium phosphate-based materials. The chemical bonding between bone and hydroxyapatite implant is accomplished by extensive bone remodeling that occurs after immature bone fills the space between bone and hydroxyapatite after implantation, and the immature bone is later replaced with mature bone. However, since hydroxyapatite and calcium phosphate have poor mechanical properties, they have a limitation in that they are difficult to apply to a load-bearing site.

In one specific embodiment of the present invention, as a result of the tensile strength test of a PEEK implant, a titanium implant, a hydroxyapatite implant, and an implant including the glass ceramic of the present invention, it was confirmed that the implant of the present invention was osseointegrated with the highest strength which suggests that the implant of the present invention overcame the limitations of the existing bone materials capable of osseointegration.

Even another aspect of the present invention provides a method for manufacturing the implant.

The method for manufacturing the implant of the present invention may include the steps of: preparing the glass ceramic composition; forming the glass ceramic composition; and heat-treating the formed glass ceramic composition.

The glass ceramic composition may be a glass ceramic composition of the present invention described above.

The method for manufacturing the implant of the present invention may include the steps of: melting the glass ceramic composition; rapidly cooling the glass ceramic composition; and pulverizing the glass ceramic composition, after preparation of the glass ceramic composition.

Specifically, the melting step of the glass ceramic composition may be performed at 1000° C. or more, 1100° C. or more, 1200° C. or more, 1300° C. or more, or 1400° C. or more, and the step of rapidly cooling the glass ceramic composition may be performed by rapidly cooling the melted glass ceramic composition, but is not limited thereto.

In one specific embodiment of the present invention, a glass ceramic composition may be prepared by mixing $SiO_2$, $Ca(OH)_2$, $CaF_2$, $B_2O_3$, MgO, and hydroxyapatite in powder form, and then, melting the prepared glass-ceramic composition at a high temperature of 1400° C. or higher for 2 hours or more, and subsequently, rapidly cooling and pulverizing the composition, thereby preparing a glass powder raw material, and the glass powder raw material prepared in this way can be used for manufacturing an implant.

The forming step of the glass ceramic composition may be performed in the same manner as a general method for manufacturing a ceramic formed body known in the art. For example, it may be performed by cold isotropic compression, hot isotropic compression, injection molding, etc., but is not particularly limited thereto.

The heat treatment step may be performed at 500° C. or higher, specifically, at 550° C. or higher, 600° C. or higher, 650° C. or higher, and 1400° C. or lower, 1300° C. or lower, 1200° C. or lower, but not limited thereto. The heat treatment step may be performed in one step or two or more steps, and when performed in two or more steps, the first heat treatment may be performed at a relatively low temperature, for example, 600 to 800° C., and then the second heat treatment may be performed at 900° C. or higher.

The method for manufacturing the implant of the present invention may further include a machining step, and the machining step may be a grinding step or a CAD/CAM step. The machining step may be performed after the heat treatment step, but is not particularly limited thereto, and may be performed before the heat treatment step or performed in the middle of several heat treatment steps.

As used herein, the term "grinding machining" refers to a precise machining operation by the relative motion of a processed product under high-speed rotation using a grinding wheel. The grinding wheel is composed of particles, conjugates, and pores. Continuous machining and efficient grinding are possible.

In one specific embodiment of the present invention, the glass ceramic composition was melted at a high temperature of 1400° C. or higher for 2 hours or more and then rapidly cooled to prepare a glass powder raw material. Then, the prepared glass powder was granulated and formed by way of a method known in the art, and then sintered at 950° C. to 1100° C. to manufacture an implant through the grinding machining.

As used herein, the "CAD/CAM" refers to the work of designing and manufacturing a prosthesis based on a computer after converting an impression body into digital data by scanning the impression body without directly scanning the structural body or making a plaster model without using an impression material. It can be applied to the production of surgical guides, customized abutments, and final implant prostheses when manufacturing implants.

In one specific embodiment of the present invention, the glass ceramic composition was melted at a high temperature of 1400° C. or higher for 2 hours or more and then rapidly cooled to prepare a glass powder raw material. Then, the prepared glass powder was granulated and formed by way of a method known in the art, then pre-sintered by the first heat treatment at 650° C. to 750° C., followed by CAD/CAM processing and the second heat treatment at 950° C. to 1100° C. to achieve complete sintering to thereby manufacture an implant.

MODE FOR CARRYING OUT THE INVENTION

Hereinafter, the present invention will be described in more detail by way of Examples. However, these Examples are provided for illustrative purposes only, and the scope of the invention is not intended to be limited to or by these Examples.

Example 1: Preparation of Glass Ceramic Composition

The glass ceramic composition of the present invention was prepared by mixing $SiO_2$, $Ca(OH)_2$, $CaF_2$, $B_2O_3$, MgO, and hydroxyapatite in powder form. Specifically, each raw material was mixed in the following amount: $SiO_2$ in an amount of 25% to 35% by weight, $Ca(OH)_2$ in an amount of 28% to 32% by weight, $CaF_2$ in an amount of 0.1% to 3% by weight, $B_2O_3$ in an amount of 0.05% to 2% by weight, MgO in an amount of 1% to 10% by weight, and hydroxyapatite in an amount of 25% to 35% by weight.

Example 2: Preparation and Composition Analysis of Crystallized Glass Ceramic

The glass ceramic composition prepared in Example 1 was melted at a high temperature of 1400° C. or higher for 2 hours or more and then rapidly cooled to prepare a glass powder raw material, and subsequently, the thus-prepared glass powder was formed in the same manner as in the general method for manufacturing a ceramic formed body known in the art, and sintered at a high temperature of 1050° C. to 1100° C. and crystallized with a purity of 99% or more.

The XRD measurement results of the crystallized glass ceramic obtained by crystallization were analyzed, and as a result, it was confirmed that wollastonite, hydroxyapatite, and diopside were present at a weight ratio of 15 to 25:50 to 60:20 to 30, as the crystalline phases of the glass ceramic. Specifically, it was confirmed that wollastonite, hydroxyapatite, and diopside were present at a weight ratio of 20:53:26 (FIG. 1).

Example 3: Preparation and Composition Analysis of Crystallized Glass Ceramic Using Glass Ceramic Composition Further Containing Na Except for using the glass ceramic composition further containing 0.42% by weight of Na in the glass ceramic composition of Example 1 based on the total weight of the glass ceramic composition, and setting the sintering temperature to 900° C. to 1100° C., a crystallized glass ceramic was prepared in the same manner as in Example 2.

The XRD measurement results of the thus-prepared crystallized glass ceramic were analyzed using the JADE program. As a result, it was confirmed that wollastonite, hydroxyapatite, and diopside were present at a weight ratio of 20:53:26 as in the crystallized glass ceramic of Example 2 as the crystalline phases of the glass ceramic.

Comparative Example 1: Preparation of Crystallized Glass Ceramic Sintered at Low Temperature A crystallized glass ceramic was prepared in the same manner as in Example 2, except that the sintering temperature was set to 970° C.

Experimental Example 1: Evaluation of Sintering Properties According to Whether Glass Ceramic Composition Contains Na In order to evaluate the sintering properties according to whether the glass ceramic composition contains Na, the crystallized glass ceramics of Examples 2, 3, and Comparative Example 1 were analyzed through XRD. The results are compared and shown in FIG. 2.

As can be seen in FIG. 2, the crystallized glass ceramic of Example 2 sintered at 1050° C. showed a wollastonite peak at 2θ (Theta) 30.0° and diopside peaks at 29.8° and 35.0°. However, the crystallized glass ceramic of Comparative Example 1 sintered at 970° C. showed a $SiO_2$ peak at 2θ 30.5°, but did not show a wollastonite peak at 2θ 30.0° and diopside peaks at 29.8° and 35.0°, confirming that no phase transformation into wollastonite and diopside was observed.

Meanwhile, it was confirmed that the crystallized glass ceramic of Example 3 prepared using the glass ceramic composition further containing Na exhibited wollastonite and diopside peaks even when sintered at 970° C. Although not delineated in any particular theory, this suggests that Na may have a role of accompanying the phase transitions to wollastonite and diopside at low temperature.

Based on these results, it was confirmed that when the glass ceramic composition further containing Na was used, glass ceramics including wollastonite, hydroxyapatite, and diopside can be prepared by sintering at a lower temperature.

Experimental Example 2: Confirmation of Processability of Glass Ceramic Composition In order to confirm the excellent processability of the glass ceramic composition according to the present invention, grinding machining and CAD/CAM machining were performed.

Experimental Example 2-1: Manufacturing of Implants for Bone Replacement Through Grinding Machining The glass ceramic composition prepared according to Example 1 was melted at a high temperature of 1400° C. or higher for 2 hours or more and then rapidly cooled to prepare a glass powder raw material. Subsequently, the prepared glass powder was granulated and formed by way of a method known in the art, and then sintered at 650° C. to 750° C. Thereafter, an implant was manufactured through grinding machining. As a result, the manufactured implant is as shown in FIG. 3*a*.

Table 1 shows the evaluation of the physical properties of the implant manufactured through the grinding machining.

TABLE 1

| Category | Target values | Experiment values | Method |
|---|---|---|---|
| Compressive strength | 3 kN or more | 14.34 ± 1.40 kN | ASTM F2077-18 |
| Torsional strength | 0.6 Nm or more | 8.22 ± 0.48 Nm | ASTM F2077-18 |
| Fatigue compressive strength | will withstand a fatigue load of 3 kN until 5,000,000 cycles without breaking | Not Broken | ASTM F2077-18 |

As shown in Table 1, it was confirmed that the implant including the glass ceramic of the present invention showed the physical properties of a compressive strength of 10 kN to 20 kN, a torsional strength of 5 Nm to 10 Nm, and a fatigue compressive strength which can withstand a fatigue load of 3 kN until 5,000,000 cycles without breaking, which exceeded the target values.

Experimental Example 2-2: Manufacture of Implants for Bone Replacement Through CAD/CAM The glass ceramic composition was melted at a high temperature of 1400° C. or higher for 2 hours or more and then rapidly cooled to prepare a glass powder raw material. Then, the prepared glass powder was granulated and formed by way of a method known in the art, then pre-sintered by the first heat treatment at 650° C. to 750° C., followed by CAD/CAM processing and the second heat treatment at 950° C. to 1100° C. to achieve complete sintering to thereby manufacture an implant. The hardness of the glass ceramic composition of the present invention after the first heat treatment and the second heat treatment is shown in FIG. 4. As shown in FIG. 4, the glass ceramic composition of the present invention exhibited a hardness of gypsum when subjected to the first heat treatment at a relatively low temperature, which is an advantageous characteristic that facilitates processing into various shapes. Due to this characteristic, after processing the glass ceramic composition subjected to the first heat treatment into a desired shape, it is possible to manufacture an implant having desired physical properties via the second heat treatment at a relatively high temperature.

The finally manufactured implant is shown in FIG. 5, and the evaluation of the physical properties of the implant manufactured through the CAD/CAM is shown in Table 2.

TABLE 2

| Category | Target values | Experiment values | Method |
|---|---|---|---|
| Compressive strength | 3 kN or more | 9.94 ± 0.90 kN | ASTM F2077-18 |
| Torsional strength | 0.6 Nm or more | 4.07 ± 0.71 Nm | ASTM F2077-18 |
| Fatigue compressive strength | will withstand a fatigue load of 3 kN until 5,000,000 cycles without breaking | Not Broken | ASTM F2077-18 |

As shown in Table 2, it was confirmed that the implant including the glass ceramic of the present invention showed the physical properties of a compressive strength of 5 kN to 15 kN, a torsional strength of 3 Nm to 7 Nm, and a fatigue compressive strength which can withstand a fatigue load of 3 kN until 5,000,000 cycles without breaking.

Based on these results, the glass ceramic composition of the present invention can be processed into an implant having excellent physical properties in all aspects including compressive strength, torsional strength, and fatigue compressive strength through grinding after sintering. In addition, it was confirmed that the glass ceramic composition can be processed into an implant having excellent physical properties even after CAD/CAM machining in the pre-sintered state, followed by complete sintering, which suggests that the glass ceramic composition of the present invention exhibits excellent processability.

Experimental Example 3: Confirmation of Physical Properties of Crystallized Glass Ceramic In order to confirm the excellent physical properties of the crystallized glass ceramic according to the present invention, the bending strength and compressive strength of the crystallized glass ceramic of Example 3 and the hydroxyapatite sintered body were measured.

The hydroxyapatite sintered body was prepared by granulating and forming by way of a method known in the art, followed by heat treatment at 1250° C.

The bending strength and compressive strength of the crystallized glass ceramic of Example 3 and the prepared hydroxyapatite were processed according to the ASTM-C674 and ASTM-C773 methods and then measured, and the results are shown in Table 3. For comparison, the bending strength and compressive strength of apatite-wollastonite (AW) glass, a representative bioactive glass, are shown together (T. Kokubo et al., *Journal of Materials Science*, 1985, pp. 2001-2004).

TABLE 3

| Category | Crystallized glass ceramic of example 3 | Hydroxyapatite | AW Glass |
|---|---|---|---|
| Bending Strength (MPa) | 240~250 | 115 | 215 |
| Compressive strength (MPa) | 1115~1320 | 830 | 1060 |

It was confirmed that the crystallized glass ceramic of the present invention had relatively high bending strength and compressive strength compared to those of the hydroxyapatite sintered body and apatite-wollastonite (AW) glass. Specifically, it was confirmed that the bending strength of the hydroxyapatite was 115 MPa and of AW glass was 215 MPa, whereas the bending strength of the crystallized glass ceramic of the present invention was 240 MPa to 250 MPa. It was also confirmed that the compressive strength of the hydroxyapatite was 830 MPa and that of AW Glass was 1060 MPa, whereas the compressive strength of the crystallized glass ceramic of the present invention was 1115 MPa to 1320 MPa (Table 3).

Based on these results, it can be found that the glass ceramic of the present invention has excellent physical properties of high strength.

Experimental Example 4: Confirmation of Bone Integration Ability of Glass Ceramic of Present Invention In order to confirm the excellent early bone integration ability of the crystallized glass ceramic of the present invention, a simulated body fluid (SBF) immersion test and an in vivo bone integration test were performed.

Experimental Example 4-1. Simulated Body Fluid Immersion Test

Since bone integration of glass ceramic is achieved through apatite formation by reaction with a body fluid, in order to evaluate the early bone integration ability of the crystallized glass ceramic of the present invention, the glass ceramic of Example 3 was immersed in a simulated body fluid, and then the formation of apatite was observed through FE-SEM (Field Emission Scanning Electron Microscope) and confirmed via EDS (Scanning Electron Microscopy) analysis and X-ray analysis.

The simulated body fluid contains $Na^+$, $K^+$, $Ca^{2+}$, $Mg^{2+}$, $Cl^-$, $HCO_3^-$, $HPO_4^{2-}$, $SO_4^{2-}$ ions, and the concentration of each ion is shown in Table 4 below.

TABLE 4

| | |
|---|---|
| $Na^+$ | 142 mM |
| $K^+$ | 5 mM |
| $Ca^{2+}$ | 2.54 mM |
| $Mg^{2+}$ | 1.54 mM |
| $Cl^-$ | 147.94 mM |
| $HCO_3^-$ | 4.2 mM |
| $HPO_4^{2-}$ | 1 mM |
| $SO_4^{2-}$ | 0.5 mM |

After the crystallized glass ceramic of the present invention was brought into contact with 50 mL of the simulated body fluid at 36.5° C., it was observed through FE-SEM and analyzed via EDS analysis and X-ray analysis.

As a result of observation through FE-SEM, it was confirmed that a gray reaction layer was formed on the surface of the crystallized glass ceramic after 10 days of exposure to the simulated body fluid (FIG. 6a).

Additionally, as a result of the EDS mapping analysis of the elements of the reaction layer formed on the surface through FE-SEM, it was confirmed that while P increased in the surface layer, Si decreased (FIG. 6b). Among the crystalline phases of wollastonite ($CaSiO_3$), hydroxyapatite ($Ca_{10}(PO_4)_6(OH)_2$), and diopside ($CaMgSi_2O_6$) present in the crystallized glass ceramic, considering that other crystalline phases do not contain P, except apatite, an increase in P and a decrease in Si in the reaction layer formed on the surface mean that apatite was formed in the reaction layer.

Meanwhile, the EDS line scan result is shown in FIG. 6c in a direction perpendicular to the surface of the glass ceramic (yellow line). A clear increase in P and decrease in Si were confirmed once again in the reaction layer position.

Furthermore, as a result of analyzing the XRD patterns of the crystallized glass ceramic after 30 days' exposure to the simulated body fluid, it was confirmed that the peak of hydroxyapatite was clearly increased, and based on the result, it was clearly confirmed that apatite was formed on the surface of the crystallized glass ceramic of the present invention (FIG. 6d). This suggests that the crystallized glass ceramic of the present invention will exhibit excellent osseointegration ability.

Experimental Example 4-2. Comparison Test of In Vivo Bone Integration in Small Animals The crystallized glass ceramic of Example 3 was processed into a long cylindrical bar with a diameter (ϕ) of 4 mm and a length of 5 mm connected to a cylindrical bar with a diameter of 6 mm and a length of 7 mm to prepare an implant including the glass ceramic of the present invention. The thin side (φ4 mm) was inserted into the iliac bone, and the thick side (φ6 mm) was placed in contact with the iliac surface. The processed bar was washed in an ultrasonic cleaner and dried at 100° C. The bar was sterilized with EO gas.

Titanium alloy implants (Ti-6al-4V, Carpenter Technology Co., Wyoming, USA), PEEK implants (PEEK-CLAS SIX, Invibio Ltd., Lancashire, UK), and hydroxyapatite (HA) implants were also prepared in the same manner as above.

According to a known method, an in vivo bone integration test was performed on the crystallized glass ceramics. Four types of implants (implant including the glass ceramic of the present invention, titanium implant, PEEK implant, and HA implant) were inserted to each rabbit (New Zealand white male rabbit with an average weight of 3.2±0.3 kg) using a predetermined rotational sequence. After the implant was inserted, the fascia tissue layer was rearranged, washed, and then sutured. For the tensile test, after sacrificing the rabbits, the iliac bone was wound with a stainless steel wire and put into the hole of the implant, so that the wire was perpendicular to the longitudinal axis of the implant. The tensile test was carried out by applying a load-cell calibrated with an Instron testing machine (Daekyung Tech co, DTU-900Mh (200 kN), Korea).

Tissue analysis was performed by removing the bone-implant block and fixing it in formaldehyde, followed by preparing a non-demineralized section and staining it with H & E, and photographing the bone-implant slide with an electron microscope (Olympus BX51TF, Japan). Histomorphometric analysis of bilateral corneal implant was performed after scale correction using a morphometric program (LEICA IM50 Image Manager, version 4.0).

As a result of measuring tensile strength (N), the average tensile strength (100 N to 150 N) of the implant including the glass ceramic of the present invention was significantly higher than the tensile strength of titanium plant (30 N to 50 N), PEEK implant (10 N to 15 N), and HA implant (70 N to 85 N) ($p>0.05$).

Additionally, as a result of tissue analysis, clear and sharp lines were observed at the bone/implant boundary in the optical microscopic analysis of the cross-sections of the polished PEEK and titanium implant cross-sections. In contrast, it was observed that the cross-section of the HA implant and the implant including the glass ceramic of the present invention was in direct contact, and the ratio was higher than that of titanium and PEEK. In addition, direct contact between the bone and the implant was observed in the HA implant and the implant including the glass ceramic of the present invention, and no surface debris or suspended particles were observed in the surrounding tissue.

Through the tensile strength test and tissue morphological analysis results, it was confirmed that the implant including the glass ceramic of the present invention binds with higher affinity than PEEK, titanium, and HA.

Based on these results, it is suggested that the implant of the present invention has excellent bone bonding properties.

Experimental Example 4-3. Human Clinical Test for Comparison of Bone Integration In order to confirm the clinical efficacy of the implant including the glass ceramic of the present invention, a comparative test was performed with a titanium cage widely used in interbody fusion surgery. The comparative test is a randomized, multicentered, single-blinded, and comparator-controlled non-inferiority test method.

The spinal fusion rate, sedimentation area, and osteolysis degree of the implant including the glass ceramic of the present invention and the titanium cage were evaluated through radiation and 3D computed tomography.

The spinal fusion rate, sedimentation area, and osteolysis degree of the implant including the glass ceramic of the present invention and the titanium cage were evaluated through radiation and 3D computed tomography.

As a result of measuring the bone integration by simple radiography and CT scan, the implant of the present invention showed no significant difference with a ratio of 91% vs. 90%, compared to the titanium implant and the implant inserted with autogenous bone. In addition, it was confirmed that there was no significant difference in the sedimentation area and the osteolysis degree.

Meanwhile, it was confirmed that the implant including the glass ceramic of the present invention has a significantly higher osseointegration area than the titanium cage.

Further, it was confirmed that the implant for early osseointegration of the present invention could be used alone without a bone graft material. That is, it was confirmed that the implant of the present invention could be used alone, and when compared with the titanium implant and the implant with autogenous bone, the implant of the present invention was osseointegrated with a ratio of 91% vs. 90%, showing effects similar to the titanium implant and the implant with autogenous bone.

Based on these results, it was confirmed that the implant for osseointegration including the glass ceramic of the present invention can be osseointegrated at an excellent rate even when used alone without a bone graft material.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A glass ceramic composition comprising $SiO_2$, $Ca(OH)_2$, $CaF_2$, $B_2O_3$, MgO, and hydroxyapatite, and wherein the composition comprises $SiO_2$ in an amount of 15% to 45% by weight, $Ca(OH)_2$ in an amount of 25% to 45% by weight, $CaF_2$ in an amount of 0.01% to 3.5% by weight, $B_2O_3$ in an amount of 0.01% to 3.5% by weight of, MgO in an amount of 0.01% to 20% by weight, and hydroxyapatite in an amount of 15% to 45% by weight based on the total weight of the glass ceramic composition.

2. The glass ceramic composition of claim 1, wherein the composition further comprises Na.

3. The glass ceramic composition of claim 2, wherein the Na is contained in an amount of 0.1% to 2% by weight based on the total weight of the glass ceramic composition.

4. A method for manufacturing an implant, comprising the steps of: preparing the glass ceramic composition described in claim 1; forming the glass ceramic composition; and heat-treating the formed glass ceramic composition.

5. The method of claim 4, wherein the method further comprises the steps of: melting the glass ceramic composition; rapidly cooling the glass ceramic composition; and pulverizing the glass ceramic composition, after preparation of the glass ceramic composition.

6. The method of claim 4, wherein the method further comprises a grinding step or a CAD/CAM step.

\* \* \* \* \*